United States Patent [19]

Yu

[11] Patent Number: 5,866,346
[45] Date of Patent: Feb. 2, 1999

[54] METHODS OF USING DYNORPHINS AS LIGANDS FOR XOR1 RECEPTOR

[75] Inventor: Lei Yu, Indianapolis, Ind.

[73] Assignee: Indiana Unversity Foundation, Bloomington, Ind.

[21] Appl. No.: 881,686

[22] Filed: Jun. 24, 1997

Related U.S. Application Data

[63] Continuation of Ser. No. 534,408, Sep. 27, 1995, abandoned.

[51] Int. Cl.[6] .............................. C12Q 1/00; C12N 15/12; C07K 14/705

[52] U.S. Cl. ........................... 435/7.21; 435/6; 435/69.1; 530/350; 536/23.5

[58] Field of Search ................................ 435/7.2, 6, 7.21, 435/69.1; 530/350; 536/23.5

[56] References Cited

PUBLICATIONS

Chen et al., FEBS Letters, 347, 279–283, Jun. 1994.
Grudi et al., Proc. Natl. Acad. Sci, 90, 11429–11432, Dec. 1993.
Lachowicz et al. J. Neurochem 64:34–40, (1995).
Wick et al., Molecular Brain Research 27:37–44, (1994).
Bunzow et al., FEBS Lett. 347:284–288, (1994).
Fubuda et al., FEBS Lett. 343:42–46, (1994).
Raynor et al., Molec. Pharmac. 45:330–334, (1993).
Walker et al., Life Sci. 31:1821–1824, (1992).

*Primary Examiner*—Sally P. Teng
*Attorney, Agent, or Firm*—Imre Balogh

[57] ABSTRACT

Orphan receptor expressed in Xenopus oocytes. The coupling of the receptor to a G protein-activated $K^+$ channel was used as a functional essay in oocytcs. Endogenous opioid peptides dynorphins were found to activate the $K^+$ channel by stimulating the orphan receptor.

1 Claim, 4 Drawing Sheets

CHO-K1 Cells

HEK-293 Cells

METHODS OF USING DYNORPHINS AS LIGANDS FOR XOR1 RECEPTOR

This application is a continuation of application Ser. No. 08/534,408, filed Sep. 27, 1995, now abandoned.

BACKGROUND OF THE INVENTION

1. Field of the Invention

The present invention relates to compositions and methods for the utilization of dynorphins for mediating physiological effects that may not be mediated entirely through the kappa opioid receptor, such as biphasic antinociception effects, motor effects, immunomodulation, inflammation response and modulation on respiration and temperature control. The present invention also relates to agonists and antagonists of dynorphins that can be found using a binding assay.

2. Reported Developments

Opioid drugs have various effects on perception of pain, consciousness, motor control, mood, and autonomic function and can also induce physical dependence (Koob et al., Trends Neurosci. 15:186, 1992). The endogenous opioid system plays an important role in modulating endocrine, cardiovascular, respiratory, gastrointestinal and immune functions (Olson et al., Peptides 10:1253, 1989). Opioids exert their actions by binding to specific membrane-associated receptors located throughout the central and peripheral nervous system (Pert et al., Science 179:1011, 1973). The endogenous ligands of these opioid receptors have been identified as a family of more than 20 opioid peptides that derive from the three precursor proteins proopiomelanocortin, proenkephalin, and prodynorphin (Hughes et al., Nature 258:577, 1975; Akil, et al., Annu. Rev. Neurosci 7:223, 1984). Although the opioid peptides belong to a class of molecules distinct from the opioid alkaloids, they share common structural features including a positive charge juxtaposed with an aromatic ring that is required for interaction with the receptor (Bradbury et al., Nature 260:165, 1976).

Pharmacological studies have suggested that there are numerous classes of opioid receptors, including those designated δ, κ, and $\mu$ (Simon, Medicinal Res. Rev. 11:357, 1991; Lutz et al., J. Receptor Res. 12:267–286, 1992). The classes differ in their affinity for various opioid ligands and in their cellular distribution. The different classes of opioid receptors are believed to serve different physiological functions (Olson et al., Peptides 10:1253, 1989; Simon, Medicinal Res. Rev. 11:357, 1991; Lutz and Pfister, J. Receptor Res. 12:267–286, 1992). However, there is substantial overlap of function as well as of distribution. Biochemical characterization of opioid receptors from many groups reports a molecular mass of 60,000 Da for all three subtypes, suggesting that they could be related molecules (Loh et al., Annu. Rev. Pharmacol. Toxicol 30:123, 1990). Moreover, the similarity between the three receptor subtypes is supported by the isolation of (i) anti-idiotypic monoclonal antibodies competing with both $\mu$ and δ ligands but not competing with κ ligands ((Gramsch et al., J. Biol. Chem. 263:5853, 1988; Coscia et al., 1991) and (ii) a monoclonal antibody raised against the purified $\mu$ receptor that interacts with both $\mu$ and κ receptors (Bero et al., Mol. Pharmacol. 34:614, 1988).

Morphine interacts principally with $\mu$ receptors and peripheral administration of this opioid induce release of enkephalins. The δ receptors bind with the greatest affinity to enkephalins and have more discrete distribution in the brain than either $\mu$ or κ receptors, with high concentrations in the basal ganglia and limbic regions. Thus, enkephalins may mediate part of the physiological response to morphine, presumably by interacting with δ receptors. Despite pharmacological and physiological heterogeneity, at least some types of opioid receptors inhibit adenylate cyclase, increase K+ conductance, and inactivate $Ca^{2+}$ channels through a pertussis toxin-sensitive mechanism (Puttfarcken et al., Mol. Pharmacol. 33:520, 1988; Attali et al., J. Neurochem. 52:360, 1989; Hsia et al., J. Biol. Chem. 259:1086, 1984). These results and others suggest that opioid receptors belong to the large family of cell surface receptors that signal through G proteins (Di Chiara et al., Trends Pharmacol. Sci. 13:185–193, 1992; Loh et al., Annu. Rev. Pharmacol. Toxicol. 30:123, 1990).

Many cell surface receptor/transmembrane systems consist of at least three membrane-bound polypeptide components: (a) a cell-surface receptor; (b) an effector, such as an ion channel or the enzyme adenylate cyclase; and (c) a guanine nucleotide-binding regulatory polypeptide or G protein, that is coupled to both the receptor and its effector.

G protein-coupled receptors mediate the actions of extracellular signals as diverse as light, odorants, peptide hormones and neurotransmitters. Such receptors have been identified in organisms as evolutionarily divergent as yeast and man. Nearly all G protein-coupled receptors bear sequence similarities with one another, and it is thought that all share a similar topological motif consisting of seven hydrophobic segments that span the lipid bilayer (Dohlman et al., Annu. Rev. Biochem. 60:653–668, 1991).

G proteins consist of three tightly associated subunits, α, β and γ (1:1:1) in order of decreasing mass. Following agonist binding to the receptor, a conformational change is transmitted to the G protein, which causes the Gα-subunit to exchange a bound GDP for GTP and to dissociate from the βγ-subunits. The GTP-bound form of the α-subunit is typically the effector-modulating moiety. Signal amplification results from the ability of a single receptor to activate many G protein molecules, and from the stimulation by Gα-GTP of many catalytic cycles of the effector. All of the family of G protein-coupled receptors appear to be similar to other members of the family of G protein-coupled receptors (e.g., dopaminergic, muscalinic, serotonergic and tachykinin), and each appears to share the characteristic seven-transmembrane segment topography.

Dynorphins are a series of peptides that share sequence homology with prodynorphin (proenkephalin B). Dynorphins are known to play a role in a wide variety of physiological parameters, including pain regulation, motor activity, cardiovascular regulation, respiration, hormone balance and the response to shock or stress. They frequently modulate the activity of other opioids, rather than having direct effects themselves. Thus, they are not analgesic in brain, yet antagonize opioid analgesia in naive animals and potentiate it in opioid tolerant animals.

Better understanding of the opioid system in analgesia will help to design more specific therapeutic drugs. In the screening process of drugs the principle operation typically is: natural agonists and antagonists bind to cell-surface receptors and channels to produce physiological effects; certain other molecules bind to receptors and channels; therefore, certain other molecules may produce physiological effects and act as therapeutic pharmaceutical agents. Thus, the ability of candidate drugs to bind to opioid receptors can function as an extremely effective screening criterion for the selection of pharmaceutical compositions with a desired functional efficacy.

After the cloning of all three major types of opioid receptors, mu, delta, and kappa, a novel receptor was cloned from several species by using homology screening technique (see: Bunzo et al., FEBS Lett. 347:284–288, (1994); Wick et al., Brain Res. Mol. Brain Res. L7:44, (1994); Wang et al., FEBS Lett. 348:75–79, (1994); and Lachowicz et al., J. Neurochem. 64:34–40, (1995). The amino acid sequence of this receptor is similar to those of the opioid receptors. However, whereas the three opioid receptors share about 70% amino acid sequence similarity among themselves, there is reduced homology level at about 65% between this receptor and any of the opioid receptors (See: Chen et al., FEBS Lett. 347:279–283, (1994)). This suggests that this novel receptor may be a member of the opioid receptor family, different from the other three receptors, and was thus design including XOR1, HOR-7, LC132, XOR, Hyp8-1, ROR-C and hORL-I. In vitro and in vivo assay systems have been used to find its ligands. A synthetic non-selective opioid agonist etorphine was shown to inhibit adenylyl cyclase in CHO-K1 cells transfected with this receptor clone, and the synthetic compounds diprenorphine and naloxone antagonized the inhibitory action of etorphine (see: Mollereau et al., FEBS Lett. 341:33–38, (1994)). However, since no endogenous (naturally existing in the body) ligands have been found for this novel receptor, it remains an "orphan" receptor.

To identify endogenous ligands for an orphan receptor, one could perform receptor binding with radiolabeled compounds. This approach has been used for the identification of $5HT_{1A}$ receptor (see for example, Fargin et al., Nature 335:358–360 (1988). However, this approach is limited in its scope, since many endogenous ligands are not available in radiolabeled form. An alternative approach is to use a functional assay, in which the orphan receptor is expressed in cells and a measurable cell function is used as a readout of receptor activation, such as changes in second messenger levels or membrane currents. In this way compounds can be tested in unlabeled form and, if a proper cellular function is chosen that the orphan receptor does couple to, there is an opportunity to identify the endogenous ligands.

Xenopus oocytes have been used in many functional studies for membrane receptors and ion channels (for example by: Dascal, N. CRC Crit. Rev. Biochem. 22:317–387, (1987); and Snutch, T. P. Trends Neurosci. 11:250–256, (1988). In particular, opioid receptors have been shown to couple to a cloned G protein-activated K+ (channel (KGA) in oocytes (see for example: Dascal et al., Proc. Natl. Acad. Sci. U.S.A. 90:10235–10239, (1993) and Kavoor et al., J. Biol. Chem. 270:589–595, (1995). Because of the high degree of homology of this orphan receptor with the opioid receptors, it may also be capable of functionally coupling to KGA in Xenopus oocytes, thus constituting an assay system for identifying endogenous ligands that can activate this receptor. I took such an approach, using an opioid receptor-like orphan receptor (XOR1) cloned from rat brain (see Chen et al., FEBS Lett. 347:279–283, (1994) for oocyte expression.

SUMMARY OF THE INVENTION

This invention relates generally to methods for identifying compounds as ligands for a novel opioid receptor, termed XOR1 here, that was previously known to be an opioid receptor-like orphan receptor. The invention includes methods for using the isolated, recombinant receptor polypeptide in assays designed to select and improve substances capable of interacting with XOR for use in diagnostic, drug design, and therapeutic applications. This invention utilized a cDNA clone to express XOR in eukaryotic cells. These cells were reacted with various opioid compounds, and the effectiveness of these compounds for rendering XOR1 functional were evaluated. The invention shows that certain opioids, in particular those related to dynorphins, are effective in causing cellular responses.

Opioid drugs, such as morphine, and the endogenous opioid peptides, namely the enkephalins, endorphins, and dynorphins, exert a wide variety of physiological and behavioral effects, including effects on pain perception, mood, motor control, and autonomic functions. The endogenous opioid peptides are widely distributed in the brain and PNS. Their broad distribution in the brain suggests that they serve general roles as neurotransmitters or neuromodulators or both. They also exert unwanted side effects on the user, such as tolerance and dependence, which makes them a major class of abused drugs. The opioids and the endogenous opioid peptides exert their effects by interacting with receptors. Pharmacological studies have defined at least three classes of opioid receptors, termed $\delta$, $\kappa$ and $\mu$, that differ in their affinity for various opioid ligands and in their distribution in the nervous system.

The effects of opioid drugs were widely investigated by the prior art, especially their effects on analgesia, as briefly described hereunder.

A large number of endogenous peptides found in various regions of the central nervous system (CNS) bind to opioid receptors and exhibit analgesic opioid activity. Opioids exert analgesic effects through actions within the CNS see, e.g., Millan (1986) Pain 27:303–3471 by interacting with receptors for endogenous opioid peptides. The endogenous opioid peptides, including the enkephalins and endorphins, are involved in the mediation and control of various physiological processes, which are mediated by the specific receptors. As indicated, a number of receptor types for these peptides have been identified in the periphery and central nervous systems [CNS] based upon differential ligand binding and the pharmacological activity of receptor agonists and antagonists. Recent evidence suggests that opioid antinociception also can be initiated by activation of opioid receptors located outside of the CNS [see, e.g., Stein (1993) Anesth. Analg. 76:182–191; Stein et al (1991) The N. Engl. J. Med. 325:1123–1126; and Stein et al (1989) J. Pharm. and Exptl. Ther. 248:1269–1275].

The major function for opiates is their role in alleviating pain [analgesia]. Other areas where opiates can be used include treatment of conditions relating to gasto-intestinal [diarrhea]. To date, opiates, opioid peptides and analogs thereof, have demonstrated a varying degree of specificity and selectivity for the receptor or receptors to which they bind. The less selective and specific an opiate is for a particular receptor type or subtype the greater the chance that increased side effects from the administration of the material will be observed. When an opiate activates more than one receptor, the biological response profile for each receptor is affected, thereby potentiating a spectrum of side effects, including adverse effects, including heaviness of the limbs, flush or pale complexion, clogged nasal and sinus passages, dizziness, depression, and constipation.

Peripheral and CNS opioid receptors include the delta ($\delta$), kappa ($\kappa$) and mu ($\mu$) receptors. The $\delta$ receptor exhibits high affinity for enkephalin peptide; $\mu$ exhibits enhanced selectivity for morphine and other poly-cyclic alkaloids; and $\kappa$ exhibits relatively poor affinity for both groups of ligands and preferential affinity for the peptide dynorphin[A]. $\beta$-endorphin appears to bind equally to the $\mu$ and $\delta$ receptors.

Among the identified receptors the type designated the $\mu$ receptor is involved in gut motility, respiratory depression, miosis, analgesia and other actions. Agonizing this receptor can result in reduced gastrointestinal motility, analgesia and euphoria. Thus, opiates, such as morphine and other opiates that are administered for analgesia also have other actions, including reduced gastrointestinal motility. Opiates with $\mu$ opioid receptor affinity can produce a powerful antidiarrheal action by a local action upon the intestinal wall (Awouters et al. (1993) Digestive Dis. and Sciences 38:977–995; Awouters et al. (1983) Ann Rev. Pharm. and Toxicol. 23:279–301). This action reflects upon the antisecretory actions of the $\mu$ receptor at this site. Many agents selected for antidiarrheal activity, such as 2,2-diphenyl-4-[(4-carbethoxy-4phenyl)piperidino] butyronitrile, generically known as diphenoxylate, act via one or more of these opioid receptors, and also have undesirable central nervous system effects and abuse potential.

Because of these diverse activities and the potential for abuse, opioid drug development has been directed towards identifying compounds in which the potentially beneficial activities are separated from the activities that lead to abuse and dependence. During the mid to late 1960's, several agents derived from classes of molecules known to have opioid activity were synthesized. These agents were shown to have naloxone reversible suppressant effects upon smooth muscle bioassays and were able to readily displace opioid ligands in receptor binding assays. These results indicated that they act via direct or indirect action with opioid receptors.

To researchers it appeared that the functions of receptors $\delta$, $\mu$ and $\kappa$ do not quite satisfactorily explain certain biological effects and efforts were make to gain information to that end. The efforts of the prior art resulted in the cloning of a new opioid receptor termed variously as h ORL1, XOR1 and "orphan" receptor. Various studies were conducted to find its endogenous ligands without success.

I have now discovered that the endogenous ligands of this "orphan" receptor comprises the class of dynorphines having properties discovered during my studies which include the following.

The orphan receptor was expressed in Xenopus oocytes and in mammalian cell lines CHO-K1 and HEK-293, via coupling the receptor to a G protein-activated K+ channel in oocytes. It was found that dynorphins activated the K+ channel by stimulating the orphan receptor and the activation was dose dependent $EC_{50}$ value at 45 nM for dynorphin A; and $EC_{50}$ value at 37 nM for dynorphin A (1–13).

It was also found that 5 $\mu$M dynorphin A (1–13) inhibited the forskolin-stimulated cyclic AMP increase by 50% in CHO-K1 and 35% in HEK-243 cells. The dynorphin effect was antagonized by naloxone at high concentrations, i.e., in $\mu$M range. At 10 to 100 $\mu$M concentrations naloxone blocks the other opioid receptor effects, however, at this concentration range naloxone only partially reversed the activation of the orphan opioid receptor.

DETAILED DESCRIPTION OF THE INVENTION

Experimental Procedures

Figure 1A:
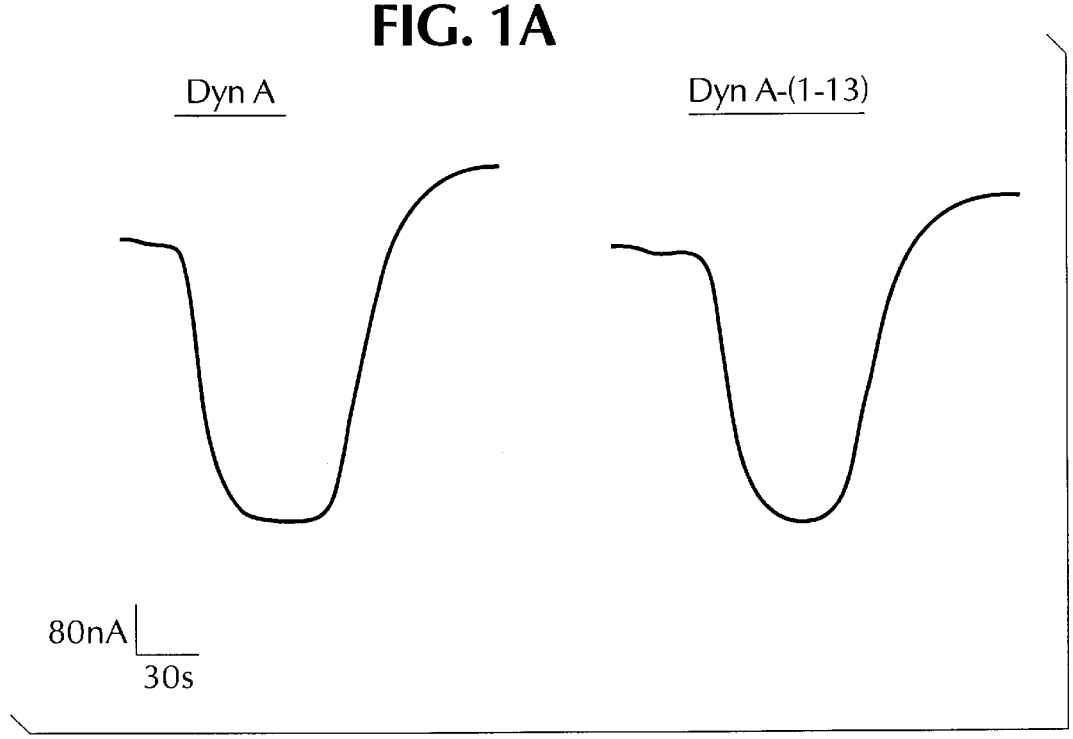
FIG. 1A and 1B: Coupling of the opioid receptor-like orphan receptor (XOR1) to a G protein-activated K+ (channel (KGA). In vitro transcribed cRNAs of XOR1 and KGA were coinjected into oocytes. Functional coupling of the receptor to the K+ channel was detected by two-electrode voltage clamp. (A) Membrane current traces recorded at a holding potential of 80 mV. Oocytes were superfused with hK solution in the presence or absence of 300 nM dyn A (left trace) or 300 nM dyn A-(1–13) (right trace) as indicated. (B) Bar graph of the membrane currents evoked by different endogenous opioid ligands at a concentration of 1 $\mu$M. Data are presented as mean ± S.E., with n of 3–8.

Materials used in the practice of the present invention and sources from which they were obtained include the following.

Opioid ligands were from Peninsula Laboratories Inc., Research Biochemicals International, Bachem Inc., and National Institute on Drug Abuse, Chinese hamster ovary cells, CHO-K1, and human embryonal kidney cells, HEK-293, cell lines were from the American Type Culture Collection. *Xenopus laevis* were from Xenopus I and African Fish Farm. Culture media were from HyClone Laboratories Inc. and Gibco BRL. In vitro transcription kit T7 mMessage mMachine was from Ambion. Cyclic AMP assay kit was from DuPont/NEN. All other chemicals were from Sigma.

Oocyte injection and Electrophysiology—Xenopus oocytes were prepared as described by Yoshii et al., J. Gen. Physiol. 90:553–573, (1987). In vitro transcribed RNA was injected into oocytes (1–2 ng/oocyte) by a Drummond automatic microinjector. Oocytes were incubated in 50% L-15 medium supplemented with 0.8 mM of glutamine and 10 μg/ml of gentamycin at 18° C. Three days after injection, oocytes were voltage-clamped at −80 mV with two glass electrodes (filled with 3 M of KCl and having a resistance of 2–3 MΩ) using an Axoclamp-2A (Axon Instruments) under the control of pCLAMP software (Axon Instruments). Oocytes were superfused with either ND96 (96 mM NaCl, 2 mM KCl, 1 mM MgCl2, 1.5 mM CaCl and 5 mM HEPES, pH 7.5) or a high potassium solution (hK: 96 mM KCl, 2 mM NaCl, 1 mM MgCl2, 1.5 mM CaCl2 and 5 mM HEPES, pH 7.5). The membrane currents were recorded with the aid of the pCLAMP software and on a Gould chart recorder.

Cell transfection and cyclic AMP assay—The CHO-K1 and HEK-293 cells were transiently transfected with either XOR1 (rat opioid receptor-like novel receptor) cDNA in pRc/CMV (Invitrogen) or vector only (as control) by calcium phosphate method as described by Chen et al., Mol. Cell Biol. 7:2745–2752 (1987). Three days after transfection, cells were harvested by trypsin treatment, washed and resuspended in serum-free medium. Cells were treated with ligands in the presence of 10 μM forskolin and 1 mM 3-iosbutyl-1-methylxanthine at 37° C. for 20 min. The reaction was terminated by adding ⅓ volume of 0.25M HCl. The mixture was boiled for 5 min and centrifuged at 14,000 g for 10 min. The supernatant was dried under vacuum and dissolved in assay buffer. The cAMP in cells was determined by the nonacetylated method using the radioimmunoassay kit (DuPont/NEN) according to the manufacturer's instructions.

Results

The orphan receptor is functionally activated by some endogenous opioid peptides—Activation of opioid receptors has been shown by their ability to couple to a cloned G protein-activated $K^+$ channel (KGA) in Xenopus oocytes (See for example: Dascal et al., Proc. Natl. Acad. Sci. U.S.A. 90:10235–10239 (1993); Chen et al., J. Biol. Chem. 269:7839–7842 (1994); Mestek et al., J. Neurosci. 15:23962406 (1995); and Kovoor et al., J. Biol. Chem. 270:589–595 (1995). Due to the sequence similarity of XOR1 to the opioid receptors, it is possible that this orphan receptor may also couple to the KGA channel in oocytes. To test this possibility, XOR1 and KGA were coexpressed in oocytes, and functional coupling of the receptor to the $K^+$ channel was assessed by two-electrode voltage clamp. Because of the high level of sequence homology between XOR1 and the opioid receptors. I examined all three classes of the endogenous opioids, dynorphins, endorphins, and enkephalins, for their ability to activate the XOR1 receptor. As shown in FIG. 1, dynorphins and some dynorphin fragments induced an inwardly rectifying $K^+$ current, presumably by stimulating the receptor coupled to KGA, while endorphins and enkephalins caused very little activation of the receptor. Oocytes injected with cRNA for XOR1 or KGA alone did not show any response to any opioid ligands (data not shown). This excluded the possibility of endogenous currents in oocytes activated by dynorphins.

Figure 1B:
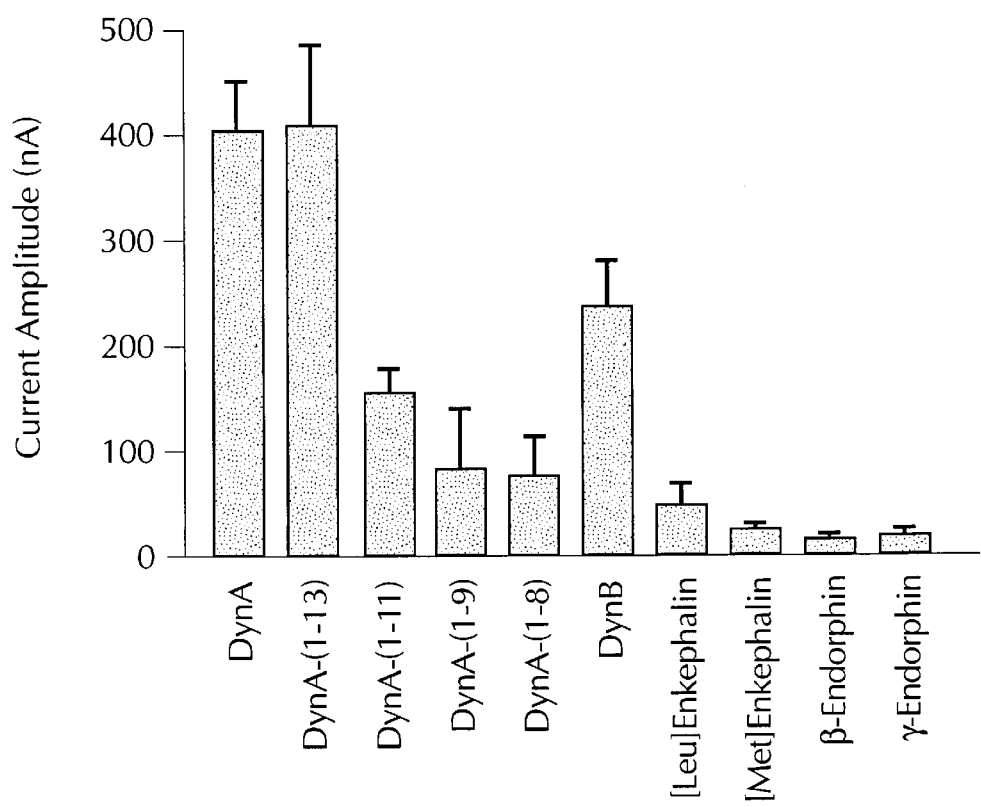

Among dynorphins, dyn A and dyn A-(1–13) are the most potent ones. FIG. 1A shows representative traces of $K^+$ currents induced by dyn A or dyn A-(1–13), a major metabolite of dyn A with physiological activity (as described by Goldstein et al., in Proc. Natl. Acad. Sci. U.S.A. 76:666&6670 (1979). The bar graph in FIG. 1B summarizes the ability of different endogenous opioid ligands to activate the orphan receptor. For dyn A and its metabolite fragments, the potency decreased with the decrease in the peptide length.

Figure 2A:
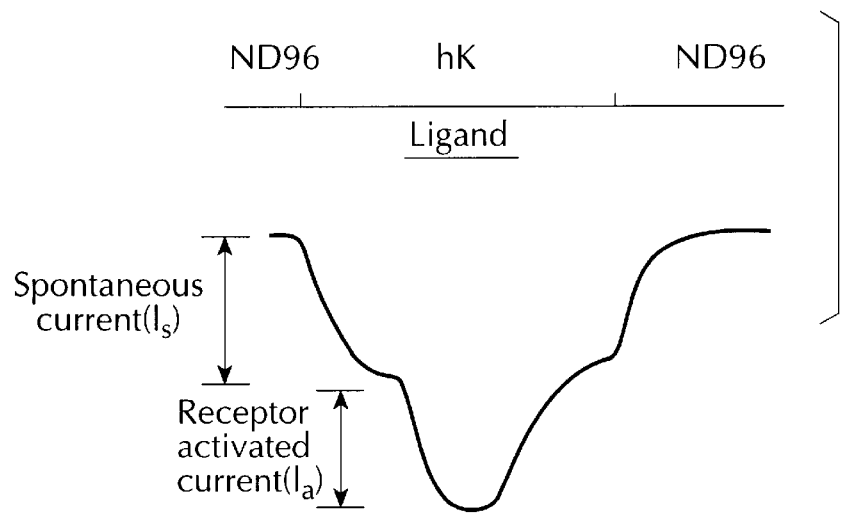
FIGS. 2A,2B, and 2C: Dose-response curves of XOR1-KGA coupling activated by dyn A and dyn A-(1–13). (A) An example of membrane current traces showing the calculation method for the ligand-evoked response. Oocytes were superfused with different solutions as indicated. Ligands were dissolved in hK solution and applied as indicated by the bar above the current trace. Spontaneous current ($I_s$) is the current when the K+ concentration is increased by switching the bath solution from ND96 to hK. Receptor-activated current ($I_a$) is the one when a ligand is applied to activate the receptor. The ratio of $I_a/I_s$ represents the extent of receptor activation by the ligand. (B) Dose-response curve of dyn A-evoked receptor activation. The results are presented as the percentage of the maximum activation. Data are mean ± S.E. (n=4–5). Each oocyte was used only once to avoid desensitization. The smooth line represents computer-aided curve fitting to the data using a simple Michaelis-Menten model. The $EC_{50}$ calculated from the curve as 45±6 nM (mean ± S.E., n=2). (C) Dose-response curve of dyn A-(1–13)-evoked activation. The $EC_{50}$ calculated from the curve as 37±9 nM (mean± S.E., n=2).
Figure 2B:
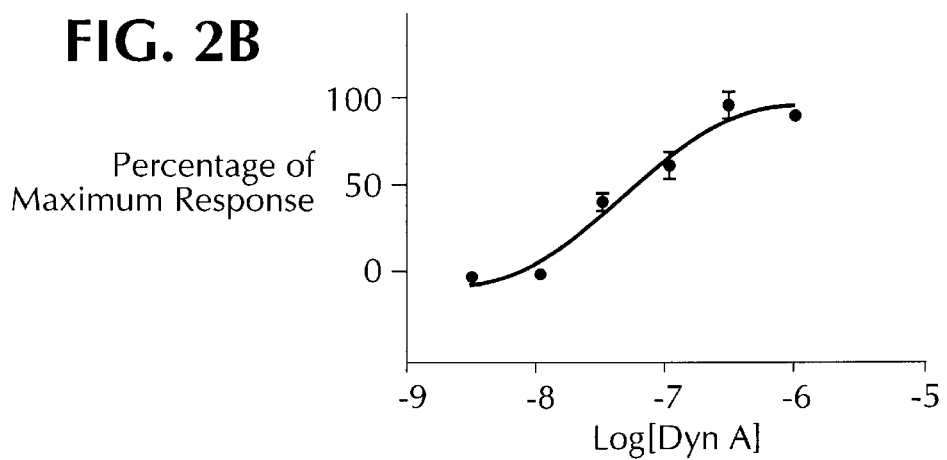
Figure 2C:
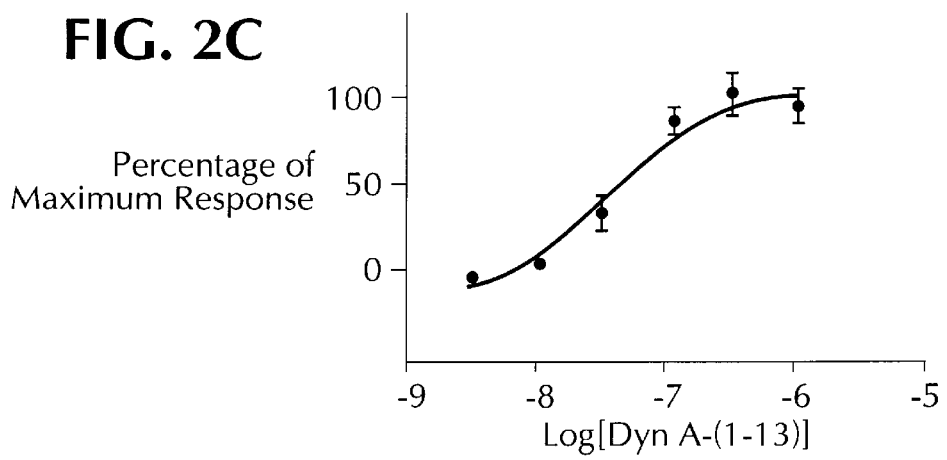

The activation of the receptor by dynorphins is dose dependent. To further study the activation of XOR1 by dynorphins, I chose the most potent peptides dyn A and dyn A-(1–13) to perform dose response experiments. Due to the variability of individual oocytes in expressing exogenous proteins, I normalized the receptor-mediated response by taking the ratio of the receptor-activated current ($I_a$) over the spontaneous current in hK solution ($I_s$), shown in FIG. 2A. As has been observed before (by Dascal et al., Proc. Natl. Acad. Sci. U.S.A. 90:10235–10239, (1993), Chen et al., J. Biol. Chem. 269:7839–7842, (1994); Mestek et al., J. Neurosci. 15:1396 2406 (1995); Kovoor et al., J. Biol. Chem. 270:589–595, (1995), and Kubo et al., Nature 364:802–806, (1993), in cells expressing the KGA channel, there is an increase in membrane $K^+$ current (the spontaneous current $I_s$) when the $K^+$ concentration in the extracellular solution is increased, such as by switching the oocyte bath solution from ND96 to hK. when the KGA channel is coexpressed with a receptor that is capable of coupling to the channel, application of an agonist for the receptor induces a receptor-activated current $I_a$ (FIG. 2A). Since both $I_a$ and $I_s$ are related to the expression level of KGA, their ratio serves as an index that is not heavily influenced by the variability in the expression level in different cells. Using this method, the dose response relations were determined for dyn A and dyn A-(1–13). As shown in FIG. 2B and 2C, both dynorphin peptides induce receptor-mediated activation of the $K^+$ channel, in a dose dependent manner. A sigmoid curve was fitted to the data for each dynorphin peptide, and an $EC_{50}$ value was calculated to be 45 nM and 37 nM for dyn A and dyn A-(1–13), respectively (FIG. 2B, 2C).

Opioid receptors are capable of regulating membrane conductance in neurons, leading to membrane hyperpolarization and decrease in neuronal firing rate or inhibition of neurotransmitter release (as shown by Duggan et al., Pharmocol. Rev. 5:219–281 (1983). The KGA has been shown to exist in the brain (as shown by Dascal et al., Proc. Natl. Acad. Sci. U.S.A. 9:10235–10239 (1993), and Kubo et al., Nature 364:802–806, (1993), and was suggested to be the $K^+$ channel mediating the neuronal effects of neurotransmitters including opioids. The functional coupling of XOR1 to KGA in Xenopus oocytes suggests that this receptor may mediate the activation of the KGA in the central nervous system and function in the neuronal regulation.

Figure 3A:
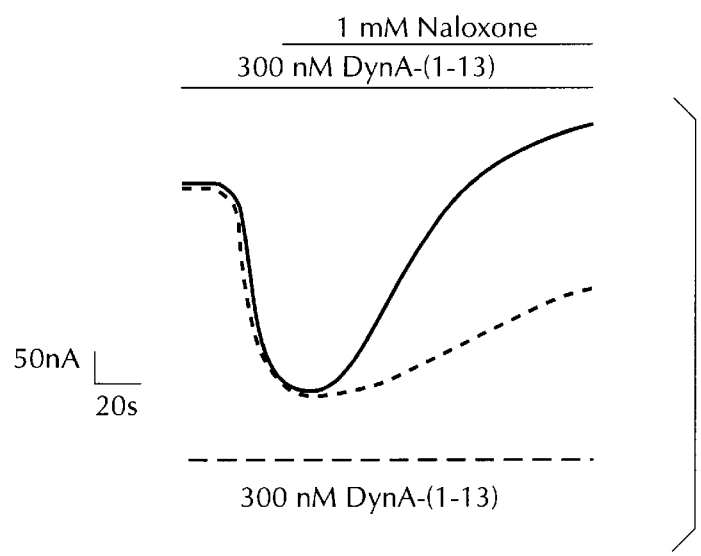
FIGS. 3A,3B, and 3C. Effect of naloxone on the activation of XOR1 by dynorphins. (A) Two representative current traces recorded with a holding potential at −80 mV. The dotted line represents a current trace induced by 300 nM dyn A-(1–13) in hK solution (broken line below the trace). The solid line was recorded with the sequential perfusion of solutions hK, 300 nM dyn A-(1–13) in hK, and 300 nM dyn A-(1–13) plus 1 mM naloxone in hK (B) Change of response evoked by 300 nM dyn A-(1–13) in the presence of different concentrations of naloxone. The data are presented as the percentage of the maximum $I_a/I_s$ (see FIG. 2 legend), shown as mean± S.E. (n =4=5). (C) Naloxone produces a rightward shift of dose-response curve for dyn A. The dose response curves were generated the same way as in FIG. 2, in the absence (●) or presence (○) of 10 $\mu$M naloxone in the dyn A-containing hK solutions. The $EC_{50}$ value for dyn A was changed from 45 nM to 372 nM by naloxone.
Figure 3B:
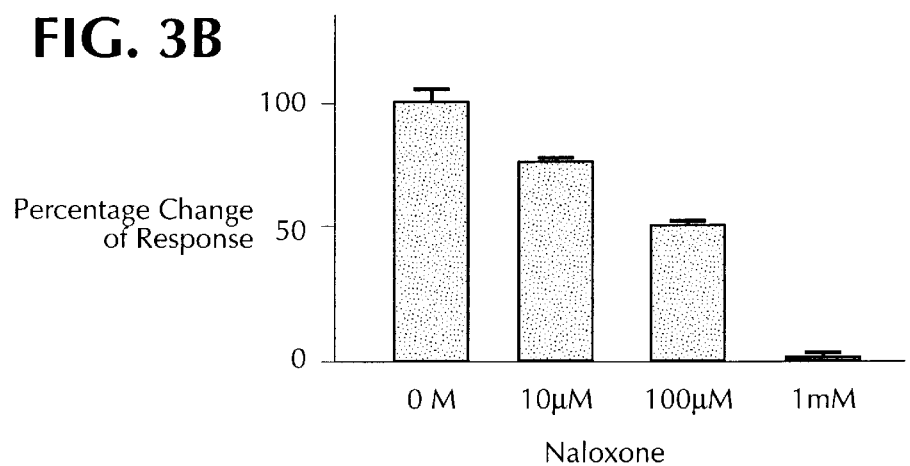

Naloxone is a low potency antagonist for XOR1— Reversibility by the non-selective opioid antagonist naloxone has been considered a major criterion for classification of an "opioid" action (as described by Lesli, F. M. Pharmacol. Rev. 39:197–249, (1987). To determine the antagonism of naloxone for XOR1, I tested naloxone in oocytes assays. As shown in FIG. 3A, after the receptor-mediated activation of the $K^+$ current by dyn A-(1–13), inclusion of 1 mM naloxone in the bath solution blocked the current. The blockade of naloxone for XOR1 activation was dose-dependent (FIG. 3B). At concentrations of 10 or 100 μM, which are enough to completely block the other opioid receptor effects, naloxone only partially reversed the activation of XOR1. At a high concentration of 1 mM, naloxone completely blocked the receptor's activation (FIG. 3A, 3B).

Figure 3C:
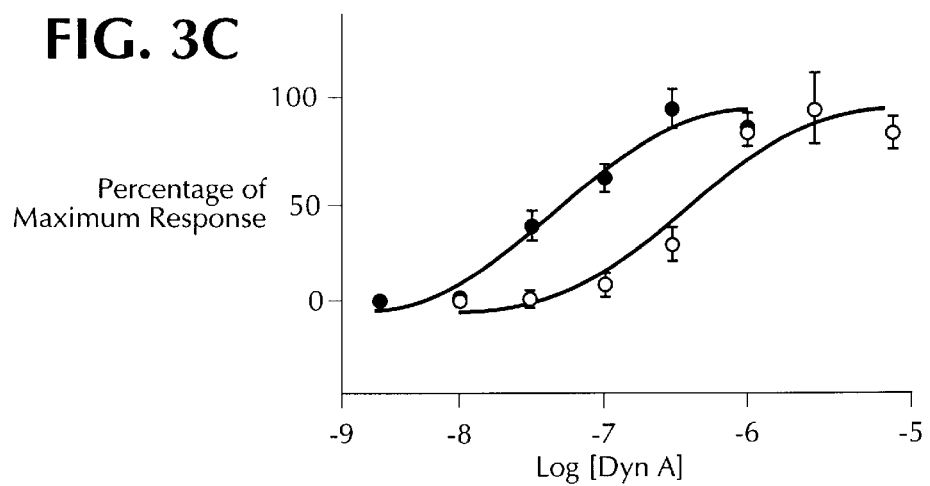

Does naloxone antagonize dynorphin effects on this receptor in a competitive manner, as for the other opioid receptors? By using naloxone with different concentrations of dyn A to perform dose response experiments, I found that 10 μM naloxone caused a parallel rightward shift of the dose-response curve for dyn A-activated response (FIG. 3C). The parallel shift of the dose response curve suggests that the antagonism by naloxone at the XOR1 receptor is competitive in nature. In this case, the $EC_{50}$ value of dyn A was shifted from 45 nM without naloxone to 372 nM with 10 μM naloxone. These data gave the apparent dissociation constant $K_e$ of naloxone for the receptor at about 1.37 μM using the Tallarida variation of Schild analysis (Tallarida et al., Life Sci. 25:637–654, (1979). Compared with the nanomolar affinity values of naloxone for mu, delta, and kappa opioid receptors (see Raynor et al., Mol. Pharmacol. 45:330–334, (1994), this value is two to three orders of magnitude higher, thus making naloxone a low potency antagonist at this novel receptor.

Figure 4A:
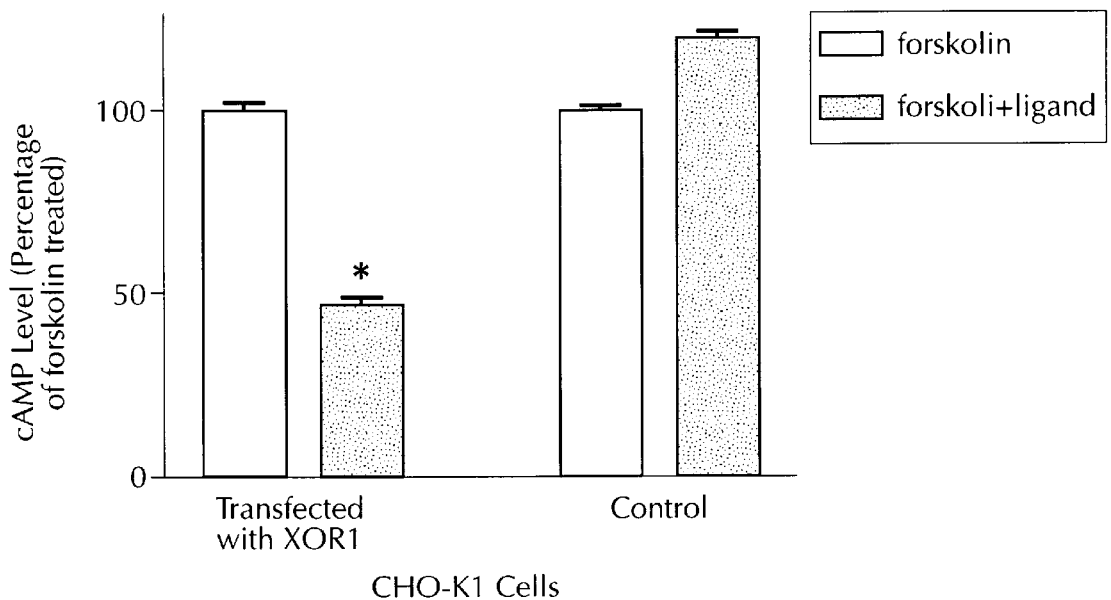
FIGS. 4A and 4B. Inhibition of forskolin-stimulated cyclic AMP increase by dyn A-(1–13). CHO-K1 or HEK-293 cells transiently transfected with the XOR1 clone were treated with 10 $\mu$M forskolin with or without 5 $\mu$M dyn A-(1–13). The control cells were transfected with the plasmid vector and underwent the same treatment. Intracellular cyclic AMP content was determined using a radioimmunoassay kit (DuPont/NEN). Data are shown as mean ± S.E. (n=2). * indicates a significant-difference from the forskolin-only treated cells (Student's t-test, p<0.01).
Figure 4B:
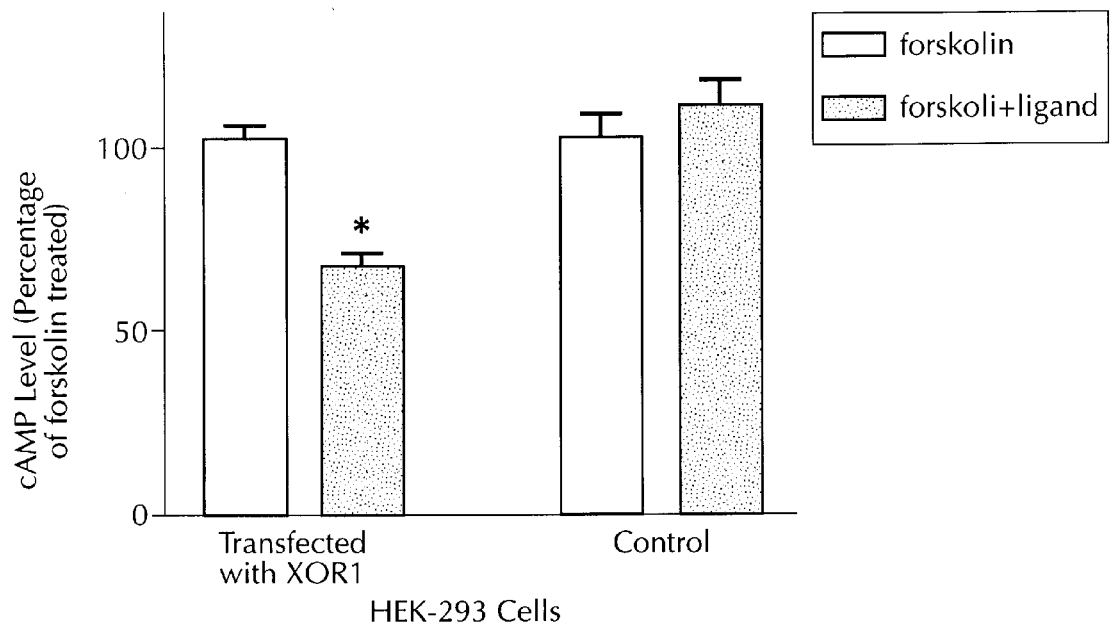

The activation of XOR1 can inhibit forskolin stimulated CAMP increase . —A hallmark of the cellular effect for all three major types of opioid receptors, mu, kappa, and delta, is that their activation results in a reduced level of intracellular cAMP (as described by Childers, S. R., Life Sci 48:1991–2003 (1991), an important second messenger in cell functions. This effect is mediated by inhibition of the adenylyl cyclase activity upon opioid receptor activation. Mammalian cells have been used as an efficient expression system for cloned opioid receptors, and it has been shown that all three cloned opioid receptors are negatively coupled to adenylyl cyclase (see: Reisine, et al., Trends Neurosci. 16:506–510, (1993)). To examine whether this novel receptor is capable of coupling to the cAMP pathway, I transiently transfected CHO-K1 and HEK-293 cells with XOR1 and tested the cAMP level after the treatment by forskolin with or without the endogenous ligands dynorphins. As shown in FIGS. 4A and 4B 5 μM dyn A-(1–13) inhibited the forskolin stimulated cAMP increase by 51% in CHO-K1, and by 35% in HEK-293, respectively. These values are significantly different from the forskolin-only treated cells ($p<0.01$), indicating that XOR1 is capable of negatively coupling to the adenylyl cyclase. The cells transfected with plasmid vector pRC/CMV alone did not show any inhibition to the cAMP increase (FIGS. 4A and 4B). Thus, like the other three major opioid receptors, mu, delta, and kappa, this novel opioid receptor also exerts an inhibitory effect on the cAMP/adenylyl cyclase pathway.

XOR1 is a novel opioid receptor distinct from the kappa opioid receptor. —The above results indicate that of the three major classes of endogenous opioid peptides, only dynorphins are capable of activating this orphan receptor, whereas the other two classes, namely endorphins and enkephalins, are not. This raises the question of whether this novel receptor is more closely related to the kappa opioid receptor, the receptor type that dynorphins interact with at high affinity (see Chavkin et al., Science 215:413–415 (1982)). To investigate this question, kappa-selective agonists were used in the oocyte functional assay. Two kappa-selective compounds, U-50,488 and U-69,593, were used, because these compounds have nanomolar affinity at the kappa opioid receptor. When applied in the bath solution to stimulate the XOR1 receptor, however, neither of the compounds induced any detectable $K^+$ current even at micromolar concentration (data not shown). Affinity values of various compounds for the cloned kappa opioid receptor have been reported, and Table I shows a comparison of these values between the XOR1 receptor and the kappa opioid receptor from rodent species. It can be seen that while dynorphins have subnanomolar affinity values at the kappa opioid receptor, its $EC_{50}$ values at this novel receptor are above 30 nM. Also, synthetic kappa-selective agonists U-50, 488 and U-69,593 do not activate this receptor. In addition, naloxone has a 1.37 μM affinity value at this receptor, whereas it displays nanomolar affinity values at the kappa opioid receptor. These data indicate that the XOR1 receptor is distinct from the kappa opioid receptor.

TABLE 1

Comparison of affinity values between the XOR1 eceptor and the kappa opioid receptor Data are expressed in nM. Sources for the kappa opioid receptor (KOR) $K_i$ values are referenced in parenthesis. N.F., no functional activation of the XOR1 receptor.

| Ligands | XOR1 | | KOR ($K_i$) | | | | | |
|---|---|---|---|---|---|---|---|---|
| | $EC_{50}$ | Ki | Rat (26) | Rat (27) | Rat (33) | Rat (34) | Mouse (23) | Mouse (35) | Guinea pig (36) |
| Dyn A | 45 | — | — | 0.15 | 0.05 | 0.11 | 0.5 | 0.4 | 0.58 |
| Dyn A-(1-13) | 37 | — | — | — | — | 0.12 | — | — | 0.71 |
| U-50,488 | N.F. | — | 5.8 | 4.8 | 2.5 | 1.9 | 0.12 | 1.1 | 1.54 |
| U-69,593 | N.F. | — | 9.0 | 7.3 | — | 2.0 | 0.59 | 2.6 | 1.37 |
| Naloxone | — | 1,376 | 20 | — | 10.5 | 9 | 2.3 | 4.9 | 11.4 |

26 = Chen et al., Biochem. J. 295: 625–628 (1993)
27 = Xue et al., Chem. 269: 30195–30199 (1994)
33 = Li et al, Biochem. J. 295: 629–633 (1993)
34 = Meng et al, Proc. Natl. Aced. Sci, U.S.A. 90: 9954–9958 (1993)
23 = Raynor et al., Mol. Pharmacol. 45: 330–334 (1994)
35 = Yasuda et al, Proc. Natl. Aced. Sci. U.S.A. 90: 6736–6740 (1993)
36 = Xie et al, Proc. Natl. Aced. Sci. U.S.A. 91: 3779–3783 (1994)

It is interesting to note that, while the overall sequence homology between this orphan receptor and each of the cloned mu, delta, and kappa opioid receptors is similar, there is apparent resemblance of the highly negative charges in the second extracellular loop between this receptor and the kappa opioid receptor. There are seven negatively charged amino acid residues in this region for both the kappa receptor and this receptor, whereas there are only two negatively charged residues in either the mu or delta receptor (see Chen et al., FEBS Lett. 347:279–283 (1994)). In opioid receptors, this loop is the longest among the three extracellular loops with a low level of sequence homology (see Chen et al, Biochem. J. 295:625–628 (1993), suggesting the possibility that it may be involved in ligand binding specificity for the receptors. Indeed, this region in the kappa receptor has been shown to be critical for high affinity binding of dynorphin peptides (see Xue et al., *Chem.* 269:30195–30199 (1994)) which are basic peptides with five positively charged amino acid residues for both dyn A and dyn A-(1–13) (see Goldstein et al., *Proc. Natl. Acad. Sci. U.S.A.* 76:6666–6670 (1979) and Goldstein et al, *Proc. Natl. Acad. Sci. U.S.A.* 78:7219–7223 (1981)). The highly negative charges in this region of the orphan receptor may contribute to the interaction between dynorphins and the receptor.

In summary, the data presented indicate that this opioid receptor-like orphan receptor is indeed a novel member of the opioid receptor family, because it can be activated by the endogenous ligands dynorphins. Similar to the other opioid receptors, this receptor also inhibits adenylyl cyclase activity. Unlike the other opioid receptors, however, naloxone does not effectively block this receptor, suggesting that it may mediate some of the "non-opioid" effects of dynorphins. Endorphins or enkephalins are rather ineffective at this receptor, whereas several of the dynorphin peptides can activate it, suggesting that there may be other dynorphin-related endogenous ligands for this receptor.

Utilities of the Present Invention

The utilities of the present invention include but are not limited to the following:

1. This invention identified endogenous compounds, i.e., opioid peptides, as ligands for an opioid receptor-like orphan receptor (termed XOR1 in this invention). Therefore, these endogenous peptides such as dynorphin A and dynorphin A-(1–13) may be used as compounds in experimental and/or therapeutic uses.

2. Other dynorphin class peptides also renders XOR1functional. Therefore, dynorphin-related peptides, i.e., those with sequence similarity to dynorphins, may also be functional and may be used for therapeutic purposes.

3. Synthetic and/or natural compounds with sequence similarities to dynorphins may be used to render XOR1 functional. Thus, possible therapeutic value.

4. XOR1 may be used to identify natural and/or synthetic compounds that bind to it and/or interact with it.

5. XOR1 may be used to test the effectiveness of natural and/or synthetic compounds that interact with it.

6. Because this invention identified XOR1 as a novel member of the opioid receptor family, reagents that affect its activity may be used to influence the opioid system in the body. Such reagents may include chemicals, peptides, and nucleic acids.

7. XOR1 may serve as a target for gene therapy to affect the opioid-involved physiology and bodily functions, such as pain sensation/perception, memory, stress, gastrointestinal motility, and immune functions.

These utilities will now be briefly discussed.

The ability to study individually the pharmacological properties of the orphan receptor will allow for identification of structural features of other ligands in addition to dynorphins I have discovered which permit selective interactions. Identification of the pharmacological interactions of drugs with the individual opioid receptors could lead to the identification of therapeutic agents less burdened with the potential to produce undesirable side effects.

In accordance with another aspect of the present invention a pharmaceutical composition is provided comprising a dynorphin and a physiologically acceptable carrier.

A composition of the present invention is typically administered parenterally in dosage unit formulations containing standard, well-known nontoxic physiologically acceptable carriers, adjuvants, and vehicles as desired. The term parenteral as used herein includes intravenous, intramuscular, intraarterial injection, or infusion techniques.

Injectable preparations, for example, sterile injectable aqueous or oleaginous suspensions, are formulated according to the known art using suitable dispersing or wetting agents and suspending agents. The sterile injectable preparation can also be a sterile injectable preparation can also be a sterile injectable solution or suspension in a nontoxic parenterally acceptable diluent or solvent, for example, as a solution is 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

A carrier can also be a liposome. Means for using liposomes as delivery vehicles are well known in the art (Gabison, et al., 1990; Ferruti, et al., 1986; Ranade 1989).

A composition of the present invention may also be administered orally. For oral administration, the pharmaceutical compositions may take the form of, for example, tablets or capsules prepared by conventional means with pharmaceutically acceptable excipients such as binding agents (for example pregelatinised maize starch, polyvinylpyrrolidone, or hydroxypropyl methylcellulose); fillers (for example, lactose, microcrystalline cellulose or calcium phosphate); lubricants (for example magnesium stearate, talc or silica); disintegrants (for example potato starch or sodium starch glycollate); or wetting agents (for example sodium lauryl sulphate). The tablets may be coated by methods well known in the art. Liquid preparation for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (for example sorbitol syrup, methyl cellulose or hydrogenated edible fats); emulsifying agents (for example lecithin or acacia); non-aqueous vehicles (for example methyl or propyl-p-hydroxybenzoates or sorbic acid).

In yet another aspect, the present invention contemplates a process of screening substances for their ability to interact with the orphan opioid receptor polypeptide, the process comprising the steps of providing the orphan polypeptide and testing the ability of selected substances to interact with that polypeptide.

Utilizing the methods and compositions of the present invention, screening assays for the testing of candidate substances such as agonists and antagonists of the orphan opioid receptor can be derived. A candidate substance is a substance which can interact with or modulate, by binding or ether intermolecular interaction, the orphan receptor polypeptide. In some instances, such a candidate substance is an agonist of the receptor and in other instances can exhibit antagonistic attributes when interacting with the receptor polypeptide. In other instances, such substances have mixed agonistic and antagonistic properties or can modulate the receptor in other ways.

Screening assays of the present invention or displacing the radioactive dynorphin generally involve determining the ability of a candidate substance to bind to the orphan receptor or to affect the activity of the orphan receptor, such as the screening of candidate substances to identify those that inhibit or otherwise modify the receptor's function. Typically, this method includes preparing the orphan receptor polypeptide, followed by testing the orphan polypeptide or cells expressing the polypeptide with a candidate substance to determine the ability of the substance to affect its physiological function. In preferred embodiments, the invention relates to the screening of candidate substances to identify those that affect the activity of the human orphan receptor, and thus can be suitable for use in humans.

As is well known in the art, a screening assay provides a receptor under conditions suitable for binding of an agent to the receptor. These conditions include but are not limited to pH, temperature, tonicity, the presence of relevant co-factors, and relevant modifications to the polypeptide such as glycosylation, palmytoilation, or prenylation. It is contemplated that the receptor can be expressed and utilized in a prokaryotic or eukaryotic cell. The host cell expressing the receptor can be used whole or the receptor can be isolated from the host cell. The receptor can be membrane bound in the membrane of the host cell or it can be free in the cytosol of the host cell. The host cell can also be fractionated into sub-cellular fractions where the receptor can be found. For example, cells expressing the receptor can be fractionated into the nuclei, the endoplasmic reticulum, vesicles, or the membrane surfaces of the cell.

pH is preferably from about a value of 6.0 to a value of about 8.0, more preferably from about a value of about 6.8 to a value of about 7.8 and, most preferably about 7.4. In a preferred embodiment, temperature is from about 20° C. to about 50° C., more preferably from about 30° C. to about 40° C. and, even more preferably about 37° C. Osmolality is preferably from about 5 milliosmols per liter (mosm/l) to about 400 mosm/l and, more preferably from about 200 milliosmols per liter to about 400 mosm/l and, even more preferably from about 290 mosm/l to about 310 mosm/l. The presence of co-factors can be required for the proper functioning of the receptor. Typical co-factors include sodium, potassium, calcium, magnesium, and chloride. In addition, small, non-peptide molecules, known as prosthetic groups can be required. Other biological conditions needed for receptor function are well known in the art.

It is well known in the art that proteins can be reconstituted in artificial membranes, vesicles or liposomes. The present invention contemplates that the orphan receptor can be incorporated into artificial membranes, vesicles or liposomes. The reconstituted orphan receptor can be utilized in screening assays.

It is further contemplated that the orphan receptor of the present invention can be coupled to a solid support. The solid support can be agarose beads, polyacrylamide beads, polyacrylic beads or other solid matrices capable of being coupled to proteins. Well known coupling agents include cyanogen bromide, carbonyldiimidazole, tosyl chloride, and glutaraldehyde.

It is further contemplated that secondary polypeptides which can function in conjunction with the receptor of the present invention can be provided. For example, the receptor of the present invention can be provided. For example, the receptor of the present invention exerts its physiological effects in conjunction with a G-protein and an effector polypeptide.

Where one uses an appropriate known ligand for the receptor, one can, in the foregoing manner, obtain a baseline activity for the orphan receptor. Then, to test for inhibitors or modifiers of the receptor function, one can incorporate into the mixture a candidate substance whose effect on the receptor is unknown. By comparing reactions which are carried out in the presence or absence of the candidate substance, one can then obtain information regarding the effect of the candidate substance on the normal function of the receptor.

Accordingly, it is proposed that this aspect of the present invention provides those of skill in the art with methodology that allows for the identification of candidate substances having the ability to modify the action of the orphan opioid receptor polypeptides in one or more manners.

In one embodiment, such an assay is designed to be capable of discriminating those candidate substances with the desirable properties of opioids but which lack the undesirable properties of opioids. In another embodiment, screening assays for testing candidate substances such as agonists and antagonists of the orphan opioid receptor are used to identify such candidate substances having selective ability to interact with one or more of the opioid receptor polypeptides but which polypeptides are without a substantially overlapping activity with other opioid receptors.

In another embodiment, the assay is used to screen for other endogenous peptides as well as agonists and antagonists thereof from medicinal chemical compound libraries.

Additionally, screening assays for the testing of candidate substances are designed to allow the investigation of structure activity relationships of opioids with the orphan receptor, e.g., study of binding of naturally occurring hormones or other substances capable of interacting or otherwise modulating with the orphan receptor versus studies of the activity caused by the binding of such molecules to the orphan receptor. In certain embodiments, the orphan polypeptide of the invention is crystallized in order to carry out x-ray crystallographic studies as a means of evaluating interactions with candidate substances or other molecules with the orphan opioid receptor polypeptide.

The detection of an interaction between an agent and the orphan receptor can be accomplished through techniques well known in the art. These techniques include but are not limited to centrifugation, chromatography, electrophoresis and spectroscopy. The use of isotopically labelled reagents in conjunction with these techniques or alone is also contemplated. Commonly used radioactive isotopes include $^3$H, $^{14}$C, $^{22}$Na, $^{32}$P, $^{35}$S, $^{45}$Ca, $^{60}$Co, $^{125}$I, and $^{131}$I. Commonly used stable isotopes include $^2$H, $^{13}$C, $^{15}$N, $^{18}$O.

For example, if an agent can bind to the orphan receptor of the present invention, the binding can be detected by using radiolabeled agent or radiolabeled receptor. Briefly, if radiolabeled agent or radiolabeled receptor is utilized, the agent-receptor complex can be detected by liquid scintillation or by exposure to X-Ray film.

The interaction of an agent and the orphan receptor can also be detected by the use of atomic force microscopy (AFM). Three dimensional images of biological materials (e.g. proteins, nucleic acids and membranes) under physiological conditions can be obtained with nanometer resolution through AFM. AFM has been used to image a number of biological specimens. (Edstrom et al., *Biophys J.* 58:1437, 1990; Drake et al., *Science* 243:1586, 1989; Butt et al., 1990; Hoh et al., 1991; Weisenhorn et al., 1990; Henderson et al., *Science* 257:1944, 1992; Hansma et al., *Science* 256:1180, 1992; Durbin and Carlson, *J. Crystal. Growth* 122:71, 1992.)

AFM operates by measuring the atomic force between the tip of an AFM probe and the top surface of the sample being imaged. The probe used for AFM is an integral part of a microfabricated cantilever, often made of $Si_3N_4$ AFM senses height of the sample surface and controls the vertical position of the sample by tracking the deflection of the cantilever. The position of the cantilever is monitored via laser beam reflection off the cantilever to an optical position sensor. The signal is used in a feedback mechanism to control the height of the sample. This feedback mechanism allows the AFM to scan over the sample surface at a constant deflection, hence a constant force. Because the atomic force is a function of inter-atomic distance, the height position of the probe represents the sample surface contour. The vertical features of the sample are thus recorded as the probe is moved over the surface in a horizontal raster scan, and the image of the sample surface can be displayed in real time during imaging and analyzed at a later time.

When an agent modifies the receptor, the modified receptor can also be detected by differences in mobility between the modified receptor and the unmodified receptor through the use of chromatography, electrophoresis or centrifugation. When the technique utilized is centrifugation, differences in mobility are known as the sedimentation coefficient. The modification can also be detected by differences between the spectroscopic properties of the modified and unmodified receptor. As a specific example, if an agent covalently modifies a receptor, the difference in retention times between modified and unmodified receptor on a high pressure liquid chromatography (HPLC) column can easily be detected.

As a specific example, where an agent covalently modifies a receptor, the spectroscopic differences between modified and unmodified receptor in the nuclear magnetic resonance (NMR) spectra can be detected. Alternatively, one can focus on the agent and detect the differences in the spectroscopic properties of the difference in mobility between the free agent and the agent after modification of the receptor.

What is claimed is:

1. A method for detecting the activation of the XOR1 receptor in cells in response to dynorphin or an analog thereof comprising the steps of:

obtaining a biological sample from a rat brain;

isolating the nucleic acid encoding the XOR1 receptor from said rat brain;

injecting the nucleic acid encoding the XOR1 receptor and the nucleic acid encoding a G-protein activated K+ channel into Xenopus oocytes;

culturing said Xenopus oocytes under conditions that allow coexpression of said XOR1 receptor and G-protein activated K+ channel;

exposing said cultured Xenopus oocytes to dynorphin or an analog thereof; and measuring the K+ currents in response to said dynorphin or analog thereof to detect activation of XOR1 receptoor.

* * * * *